United States Patent [19]

Weeks

[11] Plant 4,709

[45] May 5, 1981

[54] ROSE PLANT

[76] Inventor: O. L. Weeks, 4759 Philadelphia St., Chino, Calif. 91710

[21] Appl. No.: 142,362

[22] Filed: Apr. 21, 1980

[51] Int. Cl.[3] ..... A01H 5/00

[52] U.S. Cl. ..... Plt./20

[58] Field of Search ..... Plt./20

*Primary Examiner*—Robert E. Bagwill

*Attorney, Agent, or Firm*—Vincent G. Gioia

[57] ABSTRACT

A new hybrid tea rose variety of brilliant currant red coloring, which maintains its color upon aging and which is long lasting on the plant and as a cut flower.

1 Drawing Figure

1

The present invention relates to a new and distinct variety of rose plant of the hybrid tea rose class, which was originated by my crossing as seed parent an unnamed, unreleased seedling of my creation and the rose known as "Suspense" as pollen parent.

Among the novel characteristics possessed by this new variety which distinguish it from its parents and all other varieties of which I am aware are brilliant, substantially non-fading, currant red blooms of excellent substance which maintain color upon aging, complimented by attractive dark green waxy foliage. Flowers are exceptionally long lasting on the plant and as a cut flower. Asexual reproduction by budding of the new variety as performed in San Bernardino County, Calif., shows that the foregoing and other distinguishing characteristics come true to form and are established and transmitted through succeeding propagations.

The new and improved rose variety which I have developed is a fine hybrid tea rose with primarily singly-borne blooms with long cutting stems displayed on a vigorous upright, free branching plant with attractive dark green foliage. The flowers are of relatively heavy petalage but with excellent substance such that they are long lasting on the plant and as cut flowers.

The new variety differs from its seed and pollen parents in that the seed parent is of reddish orange coloring and the pollen parent is a bicolor while the new variety is a true non-fading red. Other distinctions are that the new variety grows more vigorously and upright than its seed parent and stronger than its pollen parent.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "47A" is plate 47A of the Royal Horticultural Society Color Chart.

Parentage: Seedling.

*Seed parent.*—Unnamed, unpatented and unreleased seedling.

*Pollen parent.*—"Suspense".

Class: Hybrid tea.

2

The following observations are made of specimens grown outdoors in San Bernardino County, Calif., during the month of October.

FLOWER

Blooming habit: Intermittent to continuous.

A. *Bud.*—(1) Size: Medium. (2) Form: Long, ovoid. (3) Color: When petals first divide — 47A. When petals begin to unfurl — 47A. (4) Petals: Simple, somewhat foliaceous, fall quickly. (5) Peduncle: Length — medium. Aspect — straight. Strength — erect. Color — reddish green 136C.

B. *Bloom.*—(1) Size: Average size when fully expanded — about 3½ to 5 inches. (2) Borne: Primarily singly on long, strong stems. (3) Form: Ovoid at first becoming loosely cupped. (4) Petalage: Number of petals under normal conditions — about 44 to 48. (5) Color: Currant red buds open to brilliant currant red blooms 47A maintaining color very well as flower matures and ages. Petals are regularly arranged and open flat giving the impression of flower fullness. Occasional white streaking of outer petals may be seen. Petaloids also appear same color 47A. Petal undersurface may appear slightly lighter 47B.

C. *Petals.*—(1) Texture: Moderately thick. (2) Appearance: Velvety. (3) Form: Obovate, round edge. (4) Arrangement: Regularly arranged. (5) Petaloids in center: Normal. (6) Persistence: Drop off cleanly. (7) Fragrance: Slight. (8) Lasting quality: Long lasting on plant and as cut flower.

REPRODUCTIVE ORGANS

A. Stamens, filaments and anthers:

(1) *Arrangement.*—Many stamens around pistils mixed with petaloids.

(2) *Color.*—Reddish yellow.

B. Pollen: Color — gold yellow.

C. Styles: Short, bunched.

D. Stigmas: Color — light purple.

E. Hips: None observed.

PLANT

A. Form: Upright.

B. Growth: Vigorous, free branching.

C. Foliage: Compound 5 to 7 leaflets.

(1) *Size.*—Large.

(2) *Quantity.*—Abundant.

(3) *Color.*—New foliage: Upper side — near to 136C. Under side — near to 191B. Old foliage: Upper side — near 133A. Under side — near 136C.

(4) *Shape.*—Ovoid, mucronate.

(5) *Texture.*—Upper side is glossy and under side is dull; leathery, somewhat wrinkled, waxy appearance.

(7) *Serration.*—Simple, fine.

(8) *Leaf stem.*—Color — near to 138A. Under side — 138A.

(9) *Stipules.*—Ordinary.

(10) *Resistance to disease.*—Mildew — good. Rust — good.

D. Wood:

(1) *New wood.*—Color — near 136C. Bark — smooth, shiny.

(2) *Old wood.*—Color — near 133A. Bark — smooth, shiny.

E. Thorns:

(1) *Thorns.*—Quantity (main stalk): many. On laterals from stalk — many. Form — hooked downward. Length — medium. Color — brown. Position — scattered, sometimes bunched.

(2) *Prickles.*—Many.

F. Winter hardiness: Good winter hardiness.

I claim:

1. A new and distinct variety of rose plant of the hybrid tea class, substantially as shown and described, characterized particularly by brilliant currant red flowers which maintain color well upon aging, borne on long stems and are long lasting on the plant and as cut flowers.

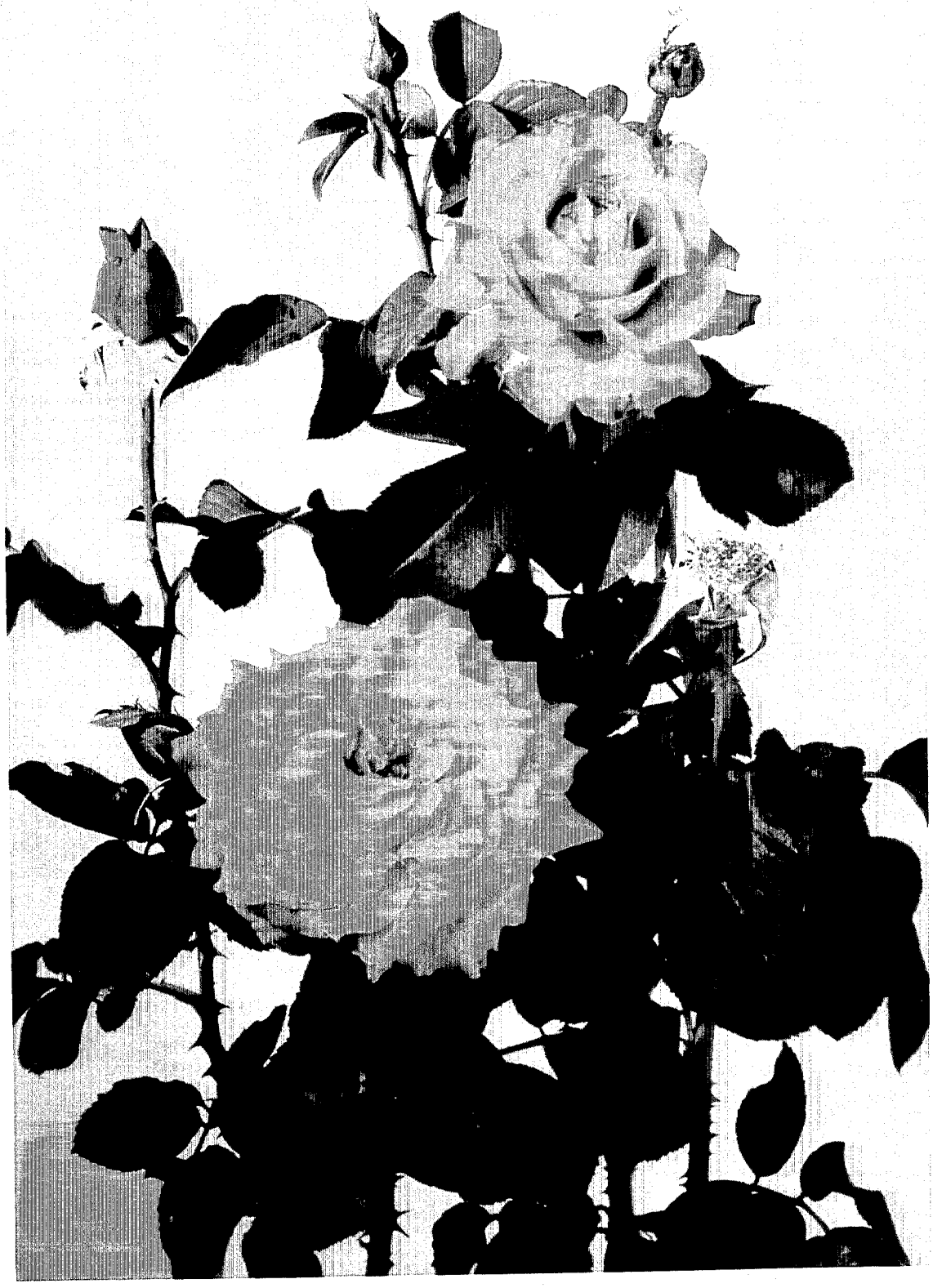

* * * * *